(12) United States Patent
Addicks et al.

(10) Patent No.: US 6,274,168 B1
(45) Date of Patent: Aug. 14, 2001

(54) PHENYTOIN SODIUM PHARMACEUTICAL COMPOSITIONS

(75) Inventors: William J Addicks; Joseph P Duda; Daniel A. Snider; Kerry R Benson, all of Morgantown, WV (US)

(73) Assignee: Mylan Pharmaceuticals Inc., Morgantown, WV (US)

( * ) Notice: Subject to any disclaimer, the term of this patent is extended or adjusted under 35 U.S.C. 154(b) by 0 days.

(21) Appl. No.: 09/255,705

(22) Filed: Feb. 23, 1999

(51) Int. Cl.[7] ............... A61K 9/20; A61K 9/48; A61K 9/16
(52) U.S. Cl. .......... 424/451; 424/464; 424/484; 424/485; 424/486; 424/487; 424/488; 424/489; 514/770; 514/772.3; 514/773; 514/774; 514/777; 514/778; 514/779; 514/781; 514/782; 514/783
(58) Field of Search ..................... 424/468, 484, 424/457, 488, 485, 486, 487, 489, 451, 464

(56) References Cited

U.S. PATENT DOCUMENTS

| 2,409,754 | 10/1946 | Henze | 260/309.5 |
| 4,642,316 | 2/1987 | Fawzi et al. | 514/398 |
| 4,696,814 | 9/1987 | Kao et al. | 424/80 |
| 4,867,985 | 9/1989 | Heafield et al. | 424/461 |
| 4,952,402 | * 8/1990 | Sparks et al. | 424/419 |
| 5,811,126 | * 9/1998 | Krishnamurthy | 424/498 |

FOREIGN PATENT DOCUMENTS

| 0563507 | 10/1993 | (EP) . |
| 9215285 | 9/1992 | (WO) . |
| 9832427 | 7/1998 | (WO) . |

OTHER PUBLICATIONS

Abu T.M. Serajuddin et al., Influence of pH on Release of Phenytoin Sodium from Slow–Release Dosage Forms, Mar. 1993, vol. 82, No. 3, pp. 306–310, J. of Pharmaceutical Sciences.

* cited by examiner

Primary Examiner—James M. Spear
(74) Attorney, Agent, or Firm—Rothwell, Figg, Ernst & Manbeck

(57) ABSTRACT

A pharmaceutical composition is provided containing an admixture of phenytoin sodium and an erodible matrix which extends the release of the phenytoin sodium over about a two hour period. The erodible matrix comprises binder(s) and diluent(s) which control the release of drug from the pharmaceutical composition. The erodible matrix can further comprise an alkaline pH modifier.

44 Claims, 2 Drawing Sheets

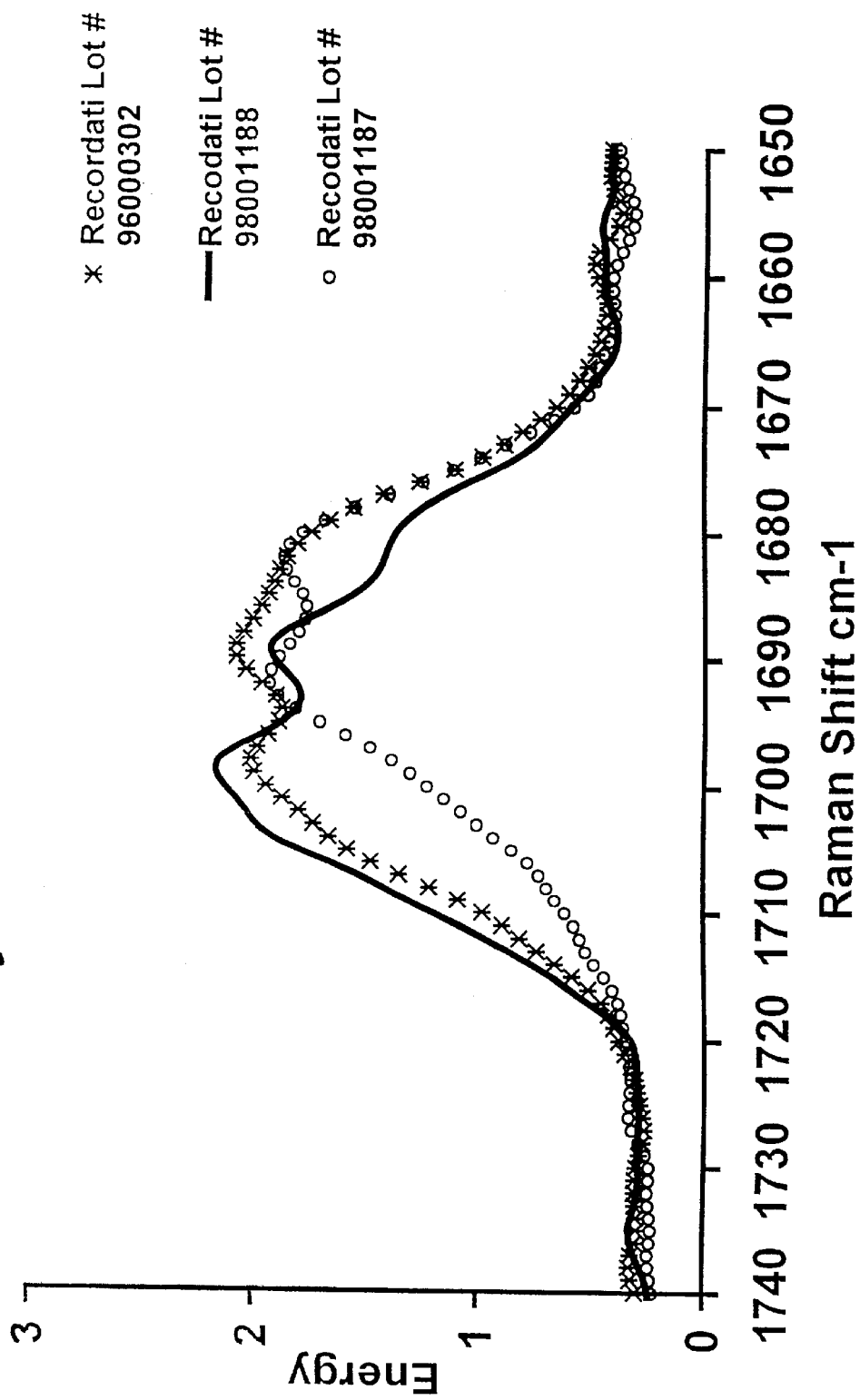

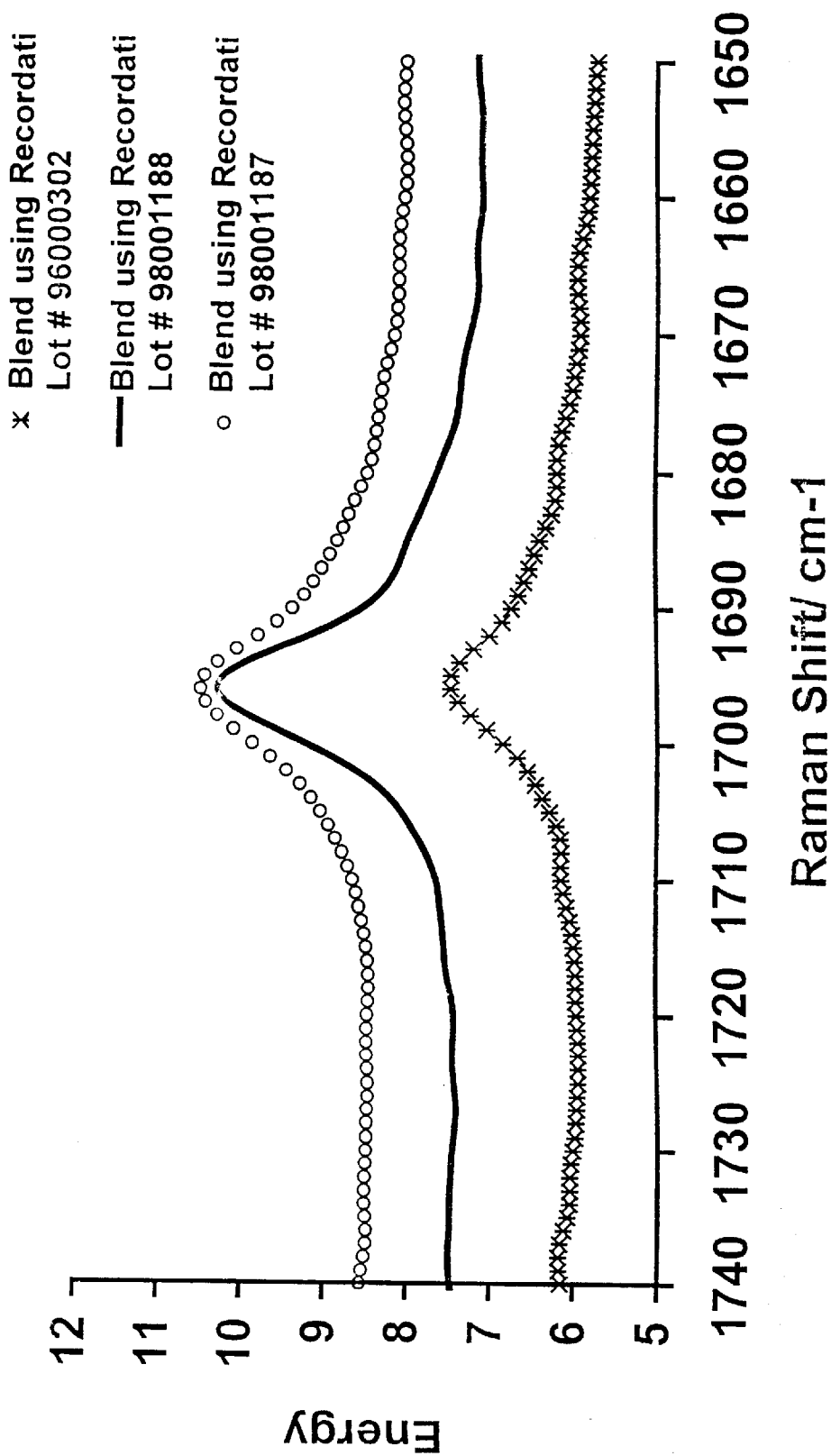

PHENYTOIN SODIUM PHARMACEUTICAL COMPOSITIONS

BACKGROUND OF THE INVENTION

1. Field of the Invention

The invention relates generally to the field of epilepsy treatment, and more particularly to antiepileptic pharmaceutical compositions for oral administration.

2. Background of the Art

Phenytoin sodium is a known antiepileptic compound. Phenytoin, phenytoin sodium, and procedures for their manufacture are well known, see for example Kao et al U.S. Pat. No. 4,696,814 issued Sep. 29, 1987; Fawzi et al U.S. Pat. No. 4,642,316 issued Feb. 10, 1987; and Henze U.S. Pat. No. 2,409,754, issued Oct. 22, 1946, all of which are incorporated herein by reference.

Phenytoin sodium is commercially available as an oral extended release pharmaceutical composition. Drug release problems associated with these pharmaceutical compositions have resulted in numerous recalls for failure to meet dissolution requirements.

Consequently, there is a need and a desire for reliable extended release phenytoin sodium pharmaceuticals.

SUMMARY OF THE INVENTION

The present invention involves an extended release pharmaceutical composition comprising an admixture of phenytoin sodium and an erodible matrix, wherein the matrix comprises a pharmaceutically acceptable binder(s), diluent (s), or combination thereof. The matrix releases the drug from the pharmaceutical composition both initially and after storage for 12 months at 25 degrees centigrade/60% relative humidity over about a two hour period when pharmaceutical compositions made from 30 to 100 mg phenytoin sodium are measured in-vitro by dissolution testing in 900 ml of water using a basket rotating at 50 rpm. The use of an erodible matrix imparts reliability to the in-vitro dissolution profile of the pharmaceutical composition of the present invention.

BRIEF DESCRIPTION OF THE DRAWINGS

The following drawings are illustrative of certain embodiments of the invention and are not meant to limit the scope of the invention as encompassed by the claims.

FIG. 1 is a graphic representation of the Raman Spectra for three different lots of phenytoin sodium raw material. The graph shows that various polymorphs of phenytoin sodium exist.

FIG. 2 is a graphic representation of the Raman spectra for the phenytoin sodium species obtained after granulation with an aqueous solvent.

DETAILED DESCRIPTION OF THE INVENTION

The extended release pharmaceutical composition of the present invention comprises an admixture of phenytoin sodium and an erodible matrix, wherein the matrix comprises a pharmaceutically acceptable binder(s), diluent(s), or combination thereof. The matrix releases the drug from the pharmaceutical composition initially and after storage for 12 months at 25 degrees centigrade/60% relative humidity over about a two hour period when measured in-vitro by dissolution testing. Pharmaceutical compositions of the present invention have the following in-vitro dissolution profile: (a.) not more than 45 percent drug released in 30 minutes, (b.)between 40 and 80 percent drug released in 60 minutes, and (c.) not less than 70 percent drug released in 120 minutes. Dissolution testing can be determined by any method known and accepted in the art. A recognized dissolution method applicable for pharmaceutical compositions made with 30 to 100 mg phenytoin sodium comprises testing in 900 ml of water using a basket rotating at 50 rpm.

Phenytoin sodium is well known and is also referred to as the monosodium salt of 5,5-diphenyl hydantoinate (phenytoin), which is described on page 1259 of the Twelfth Edition of the Merck Index, which is incorporated herein by reference. Phenytoin sodium is commercially available in several polymorphic forms, and FIG. 1 shows the Raman Shift for some of those polymorphs. In the present invention, the phenytoin sodium incorporated into the current invention can be any of the polymorphic mixtures commercially available. It has been found that the processing of polymorphic mixtures of phenytoin sodium with the component(s) of the erodible matrix yields a phenytoin species.

Phenytoin salts are water soluble whereas phenytoin is water insoluble. The solubility difference between phenytoin salts and phenytoin is an important factor when preparing pharmaceutical preparations because solubility will influence or dictate the types and amounts of other ingredients to be used in the pharmaceutical preparation. Phenytoin sodium is highly water soluble.

"Erodible matrix" is used herein to describe the part of the pharmaceutical composition which controls the dissolution release rate of the drug so that in-vitro it is released over about a two hour period. The erodible matrix is able to maintain this release rate both initially when the pharmaceutical compositions are manufactured and after the compositions have been stored for about 12 months at 25 degrees centigrade/60% relative humidity. The erodible matrix controls the release of drug either by erosion, diffusion, or a combination thereof. The advantage of using an erodible matrix delivery system admixed with phenytoin sodium, as compared to a loose powder-filled delivery system, is that the erodible matrix provides a more uniform and reproducible dissolution profile. This phenomenon may result from the fact that the drug release from the erodible matrix is dependent upon the inherent diffusion rate constant of the drug within the matrix and the rate of erosion of the matrix, instead of factors like particle size and shape, which appear to play a significant role in the release of drug from a loose, powder-filled delivery device.

Erodible matrix components include binders, diluents, and, optionally, alkaline pH modifier(s) and commonly used pharmaceutical excipients. "Binders" are compounds which cause agglomeration of drug and excipient particles during the manufacturing process and act to control the release of drug from the dosage form. The agglomeration can be in the form of a granulation or a powder. Binders can include acacia, alginic acid, carbomer, carboxymethylcellulose sodium, ethylcellulose, guar gum, hydroxypropyl cellulose, hydroxypropylmethyl cellulose, hydroxyethyl cellulose, liquid glucose, magnesium aluminum silicate, maltodextrin, methylcellulose, povidone, pregelatinized starch, sodium alginate, starch, dextrin, gelatin, hydrogenated vegetable oils, polymethacrylates, and zein. Preferred binders are povidone, hydroxyethyl cellulose, hydroxypropyl cellulose, and hydroxypropylmethyl cellulose. The most preferred binders are povidone and hydroxyethyl cellulose used in combination.

"Diluents" are compounds which possess no therapeutic value but add unique physical characteristics to a pharmaceutical composition. Diluents can include microcrystalline cellulose, powdered cellulose, lactose, starch, mannitol, dextrose, and dibasic calcium phosphate. Preferred diluents are microcrystalline cellulose, powdered cellulose, and lactose. The most preferred diluent is microcrystalline cellulose.

"Alkaline pH modifier" is used herein to describe a material which ensures that the pH of the dosage form is maintained above 8 during manufacture, storage, and administration of the pharmaceutical composition. Phenytoin salts can convert in various degrees to practically insoluble phenytoin within the pH ranges of 1 to 8. In this pH range, it is possible that a conversion occurs inside or at the surface of the pharmaceutical compositions of the present invention, thereby retarding dissolution of the active ingredient. The use of an alkaline pH modifier may make it less likely that conversion to insoluble phenytoin will occur during manufacture of the dosage form, during storage of the finished product, and following administration of the pharmaceutical composition to a human. Examples of alkaline pH modifiers may include magnesium oxide, calcium carbonate, magnesium aluminum silicates, and other mineral bases. The most preferred alkaline pH modifier is magnesium oxide.

"Commonly used pharmaceutical excipients" is used herein to include the following: (a) lubricants, e.g. talc, sodium stearyl fumarate, calcium and magnesium stearate, stearic acid, hydrogenated vegetable oil, sodium lauryl sulfate, and solid polyethyl glycols; (b) glidants, e.g. colloidal silicon dioxide, and talc; and (c) coatings and protective matrices, e.g. polymeric substances or waxes.

A dosage unit of the present pharmaceutical composition may consist of, for example, tablets, capsules, pills, pellets, slugs, spheroids, beads, or granules processed with a predetermined amount of phenytoin sodium. A dosage unit is usually prescribed to be taken by a human 1 to 4 times a day. The most preferred dosage unit is a tablet within a capsule.

Typically, the amount of phenytoin sodium used ranges from between about 5% to about 90% (weight percent) per dosage unit. Most preferably, the amount will range from between about 15% to about 75% (weight percent) per dosage unit.

Typically, the erodible matrix in accordance with the present invention is provided in an amount necessary to maintain the in-vitro dissolution rate of drug over about a two hour period. The amount of the erodible matrix will depend upon the binder(s) and diluent(s) used to form the matrix. In general, the erodible matrix is provided in an amount ranging from between about 10% to about 95% (weight percent) of the dosage unit. Most preferably, the erodible matrix is provided in an amount ranging from between about 25% to about 85% (weight percent) of the dosage unit.

In general, the contents of the erodible matrix will comprise one or more binders, one or more diluents, or a combination thereof. Preferably, the matrix will comprise about 1% to about 35% binder(s) and about 65% to about 99% diluent(s) (weight percent in the matrix). Optionally, the matrix will further comprise up to about 0.1% to about 1% glidant(s), up to about 0.5% to about 4% lubricant(s), or up to about 1% to about 10% alkaline pH modifier(s) (weight percent in the matrix). Most preferably, the erodible matrix will comprise about 5% to about 20.5% binder(s), about 68% to about 91.7% diluent(s), about 0.3% to about 0.5% glidant(s), about 1% to about 3% lubricant(s), and about 2% to about 8% pH modifier(s) (weight percent in the matrix). For particular desired embodiments, the selection of specific amounts within these ranges can be determined by those skilled in the art.

The pharmaceutical compositions according to the present invention can be prepared using conventional pharmaceutical mixers, pharmaceutical blenders, fluidized bed dryers, tray dryers, coating pans, milling devices and tablet presses. Specifically, phenytoin sodium is first mixed with diluents, binder(s), alkaline pH modifier(s), or a combination thereof, and then granulated with an aqueous solvent which may or may not contain a binder(s). Granulation is preferably carried out in a granulator, and the granulation is then dried. The presence of an adequate amount of the aqueous solvent is important to the granulation process because the water is believed to dissolve the phenytoin sodium, regardless of its polymorphic form, so that upon drying and resolidification, the resulting mixture will contain a unique phenytoin species characterized by the Raman Shift of FIG. 2. It is important that about 31 mg to about 61 mg of water be used per 100 mg of phenytoin sodium in the granulating process. The dried granulation is then milled and final blended with other excipients. The blend may then be filled into capsules or compressed into tablets. The tablets may then be additionally coated and/or filled into capsules.

The following examples further illustrate the invention and are not to be construed to limit the claims in any manner.

EXAMPLE 1

Capsules containing phenytoin sodium tablets were prepared according to the following:

| Ingredient | Amount Per Tablet |
| --- | --- |
| Phenytoin Sodium | 100.0 mg |
| Povidone | 8.5 mg |
| Hydroxyethyl Cellulose | 4.25 mg |
| Microcrystalline Cellulose | 55.15 |
| Colloidal Silicon Dioxide | 0.4 mg |
| Magnesium Stearate | 1.7 mg |

A binder solution of povidone in water was prepared. The phenytoin sodium (Recordati lot number 96000302, Allendale, N.J.), hydroxyethyl cellulose, and microcrystalline cellulose were mixed in the bowl of a granulator and then granulated with the binder solution. The resulting granulation was dried, milled, and blended with the colloidal silicon dioxide and the magnesium stearate. The blended material was then compressed into tablets using a rotary tablet press, and the tablets were placed into capsules. The capsules were packaged into high-density polyethylene bottles and stored for 3 months at 40 degrees centigrade/ 75% relative humidity and tested for dissolution at 30, 60, and 120 minutes. A summary of the dissolution data is found in Table I and II. The Raman Shift of the phenytoin sodium raw material and of the resultant phenytoin species can be found in FIGS. 1 and 2.

EXAMPLE 2

Capsules containing phenytoin sodium tablets were prepared according to the following:

| Ingredient | Amount Per Tablet |
| --- | --- |
| Phenytoin Sodium | 100.0 mg |
| Povidone | 6.8 mg |
| Hydroxyethyl Cellulose | 2.98 mg |
| Microcrystalline Cellulose | 54.12 |
| Magnesium Oxide | 4.0 mg |
| Colloidal Silicon Dioxide | 0.4 mg |
| Magnesium Stearate/Sodium Lauryl Sulfate (94/6) | 1.7 mg |

A binder solution of povidone in water was prepared. Phenytoin sodium (Recordati lot number 96000302, Allendale, N.J.), hydroxyethyl cellulose, magnesium oxide, and microcrystalline cellulose were mixed in the bowl of a granulator and then granulated with the binder solution. The resulting granulation was dried, milled, and blended with the colloidal silicon dioxide and the magnesium stearate/sodium lauryl sulfate. The blended material was then compressed into tablets using a rotary tablet press, and the tablets were then placed into capsules. The capsules were packaged into high-density polyethylene bottles and stored for 3 months at 40 degrees centigrade/75% relative humidity and 12 months at 25 degrees centigrade/60% relative humidity. These samples were tested for dissolution at 30, 60, and 120 minutes. A summary of the dissolution data is found in Table I, II, and III. The Raman Shift of the phenytoin sodium raw material and of the resultant phenytoin species can be found in FIGS. 1 and 2.

EXAMPLE 3

Capsules containing phenytoin sodium tablets were prepared according to the following:

| Ingredient | Amount Per Tablet |
| --- | --- |
| Phenytoin Sodium | 100.0 mg |
| Hydroxypropyl Cellulose | 8.5 mg |
| Hydroxypropyl Methylcellulose | 5.1 mg |
| Microcrystalline Cellulose | 54.3 |
| Colloidal Silicon Dioxide | 0.4 mg |
| Magnesium Stearate | 1.7 mg |

A binder solution of hydroxypropyl cellulose in water was prepared. Phenytoin sodium (Recordati lot number 96000302, Allendale, N.J.), hydroxypropyl methylcellulose, and microcrystalline cellulose were mixed in the bowl of a granulator and granulated with the binder solution. The resulting granulation was then dried, milled, and blended with the colloidal silicon dioxide and the magnesium stearate. The resulting blended material was tableted using a rotary tablet press, and the tablets were placed into capsules. The capsules were packaged into high-density polyethylene bottles and stored for 3 months at 40 degrees centigrade/75% relative humidity and tested for dissolution at 30, 60, and 120 minutes. A summary of the dissolution data is found in Table I and II. The Raman Shift of the phenytoin sodium raw material and of the resultant phenytoin species can be found in FIGS. 1 and 2.

TABLE I

INITIAL DISSOLUTION OF PHENYTOIN SODIUM 100 MG CAPSULES. TESTING WAS CONDUCTED IN WATER USING BASKETS AT 50 RPM.

| Example | Percent Drug Dissolved | | |
| --- | --- | --- | --- |
| Number | 30 min | 60 min | 120 min |
| 1 | 25 | 47 | 76 |
| 2 | 30 | 53 | 92 |
| 3 | 27 | 51 | 82 |

TABLE II

DISSOLUTION OE PHENYTOIN SODIUM 100 mg CAPSULES AETER STORAGE FOR THREE MONTHS AT 40 DEGREES CENTIGRADE/75% RELATIVE HUMIDITY. CAPSULES WERE PACKAGED IN HIGH-DENSITY POLYETHYLENE BOTTLES. TESTING WAS CONDUCTED IN WATER USING BASKETS AT 50 RPM.

| | Percent Drug Dissolved | | |
| --- | --- | --- | --- |
| Example Number | 30 minutes | 60 minutes | 120 minutes |
| 1 | 22 | 45 | 72 |
| 2 | 28 | 56 | 95 |
| 3 | 24 | 46 | 73 |

TABLE III

DISSOLUTION OF EXAMPLE 2 PHENYTOIN SODIUM 100 mg CAPSULES AFTER STORAGE FOR 12 MONTHS AT 25 DEGREES CENTIGRADE/60% RELATIVE HUMIDITY. CAPSULES WERE PACKAGED IN HIGH-DENSITY POLYETHYLENE BOTTLES. TESTING WAS CONDUCTED IN WATER USING BASKETS AT 50 RPM.

| Time (minutes) | Percent Drug Dissolved |
| --- | --- |
| 30 | 29 |
| 60 | 58 |
| 120 | 95 |

We claim:

1. A pharmaceutical composition comprising an admixture of phenytoin sodium and an erodible matrix, wherein said matrix comprises a pharmaceutcally acceptable binder (s), diluent(s), or combination thereof, and wherein said matrix releases said phenytoin initially and after storage for 12 months at 25 degrees centigrade/60% relative humidity over two hours when measured in-vitro by dissolution testing.

2. The pharmaceutical composition of claim 1, wherein said composition has the following in-vitro dissolution profile:
   (a.) not more than 45 percent released in 30 minutes,
   (b.) between 40 and 80 percent released in 60 minutes,
   (c.) not less than 70 percent released in 120 minutes.

3. The pharmaceutical composition according to claim 1, wherein said matrix comprises a combination of binder(s) and diluent(s) whose percents are from about 1% to about 35% binder(s) and about 65% to about 99% diluent(s) and wherein the percent is the weight percent in the erodible matrix.

4. The pharmaceutical composition according to claim 1, wherein said binder(s) is selected from the group consisting of acacia, alginic acid, carbomer, carboxymethylcellulose sodium, ethylcellulose, guar gum, hydroxypropyl cellulose, hydroxypropylmethyl cellulose, liquid glucose, magnesium aluminum silicate, cellulose, maltodextrin, methylcellulose, povidone, pregelatinized starch, sodium alginate, starch, dextrin, gelatin, hydroxyethyl cellulose, polymethacrylates, hydrogenated vegetable oil, and zein.

5. The pharmaceutical composition according to claim 1, wherein said diluent(s) is selected from the group consisting of lactose, mannitol, dextrose, sucrose, starch, powdered cellulose, microcrystalline cellulose, and dibasic calcium phosphate.

6. The pharmaceutical composition according to claim 1, wherein said matrix further comprises an amount of alkaline pH modifiers) sufficient to ensure the pH of the composition is maintained above 8 during manufacture, storage, and administration.

7. The pharmaceutical composition according to claim 6, wherein the modifiers) is present in an amount ranging from between about 1% to about 10% by weight.

8. The pharmaceutical composition according to claim 6, wherein said modifier(s) is selected from the group consisting of magnesium oxide, calcium carbonate, magnesium carbonate, and magnesium aluminum silicates.

9. The pharmaceutical composition according to claim 1, wherein said matrix is present in an amount necessary to extend the in-vitro dissolution release rate of the composition over about a two hour time period.

10. The pharmaceutical composition according to claim 6, wherein said erodible matrix is comprised of about 1% to about 35% by weight binder(s), of about 65% to about 99% by weight diluent(s), and of about 1% to about 10% by weight modifier(s).

11. The pharmaceutical composition according to claim 6, wherein said erodible matrix is comprised of about 65% to about 86% by weight microcrystalline cellulose, of about 1% to about 12% by weight hydroxyethyl cellulose, of about 1% to about 10% by weight magnesium oxide, and of about 5% to about 13% by weight povidone.

12. The pharmaceutical composition according to claim 1, wherein the phenytoin sodium comprises about 5% to about 90% (weight percent) of the pharmaceutical composition.

13. The pharmaceutical composition according to claim 1, wherein the amount of said phenytoin sodium comprises about 30 mg to about 100 mg per pharmaceutical composition.

14. The pharmaceutical composition of claim 1, wherein said composition is in the form of pellets, slugs, granules, spheroids, beads, or combinations thereof.

15. The pharmaceutical composition of claim 1, wherein said composition is in the form of tablets and capsules.

16. The pharmaceutical composition of claim 1, wherein said composition is a tablet in a capsule.

17. A pharmaceutical composition comprising a tablet in a capsule, wherein said tablet is compressed from an admixture of phenytoin sodium and an erodible matrix, wherein said matrix comprises a pharmaceutically acceptable binder (s), diluent(s), and optionally, alkaline pH modifier(s), and wherein said composition has the following in vitro-dissolution profile initially and after storage for 12 months at 25 degrees centigrade/60% relative humidity when measured in-vitro by dissolution testing:

not more than 45 percent released in 30 minutes,
between 40 and 80 percent released in 60 minutes,
not less than 70 percent released in 120 minutes.

18. The pharmaceutical composition according to claim 17, wherein the phenytoin sodium comprises about 5% to about 90% (weight percent) of the pharmaceutical composition.

19. The pharmaceutical composition according to claim 17, wherein the phenytoin sodium comprises about 15% to about 75% (weight percent) of the pharmaceutical composition.

20. The pharmaceutical composition according to claim 17, wherein the matrix is comprised of about 1% to about 35% by weight binder(s), of about 65% to about 99% by weight diluent(s), and of about 0% to about 10% by weight alkaline pH modifier(s).

21. The pharmaceutical composition according to claim 20, wherein said binder(s) is selected from the group consisting of acacia, alginic acid, carbomer, carboxymethylcellulose sodium, ethylcellulose, guar gum, hydroxypropyl cellulose, hydroxypropylmethyl cellulose, liquid glucose, magnesium aluminum silicate, maltodextrin, methylcellulose, povidone, pregelatinized starch, sodium alginate, starch, dextrin, gelatin, hydroxyethyl cellulose, polymethacrylates, hydrogenated vegetable oil, and zein.

22. The pharmaceutical composition according to claim 20, wherein said diluent(s) is selected from the group consisting of lactose, mannitol, dextrose, sucrose, starch, powdered cellulose, microcrystalline cellulose, and dibasic calcium phosphate.

23. The pharmaceutical composition according to claim 20, wherein said alkaline pH modifier(s) is present in a sufficient amount to inhibit the formation of insoluble phenytoin in said pharmaceutical composition.

24. The pharmaceutical composition according to claim 20, wherein said alkaline pH modifier(s) is selected from the group consisting of magnesium oxide, calcium carbonate, magnesium carbonate, and magnesium aluminum silicates.

25. The pharmaceutical composition according to claim 20, wherein said binder is a combination of about 5% to about 13% by weight povidone and about 1% to about 12% by weight hydroxyethyl cellulose; said diluent is about 65% to about 86% by weight microcrystalline cellulose; and said alkaline pH modifier is about 1% to about 10% by weight magnesium oxide.

26. A pharmaceutical composition comprising a tablet in a capsule, said tablet compressed from an admixture formed from mixing:

(a.) about 10% to about 75% by weight phenytoin sodium and (b.) about 25% to about 90% by weight of a combination of erodible matrix components, said components comprising:
  i) about 1% to about 5% by weight hydroxyethyl cellulose,
  ii) about 66% to about 86% by weight microcrystalline cellulose,
  iii) about 5% to about 12% by weight povidone, and
  iv) about 1% to about 7% by weight magnesium oxide,
and wherein said composition has the following in-vitro dissolution profile initially and after storage for 12 months at 25 degrees centigrade/60% relative humidity when measured in-vitro by dissolution testing:

(a.) not more than 45 percent in 30 minutes,
(b.) between 40 to 80 percent in 60 minutes,
(c.) not less than 70 percent in 120 minutes.

27. A pharmaceutical composition comprising a phenytoin species in an erodible matrix, wherein the species has the Raman Shift as set out in FIG. 2 and the matrix comprises a pharmaceutically acceptable binder(s), diluent (s), or combination thereof.

28. The pharmaceutical composition according to claim 27, wherein said matrix comprises a combination about 1% to about 35% by weight binder(s), about 65% to about 99% by weight diluent(s), and about 0% to about 10% alkaline pH modifier(s).

29. The pharmaceutical composition according to claim 27, wherein said matrix releases said phenytoin species initially and after storage for 12 months at 25 degrees centigrade/60% relative humidity over two hours when measured in-vitro by dissolution testing.

30. The pharmaceutical composition of claim 29, wherein said composition has the following in-vitro dissolution profile:
  (a.) not more than 45 percent released in 30 minutes,
  (b.) between 40 and 80 percent released in 60 minutes,
  (c.) not less than 70 percent released in 120 minutes.

31. The pharmaceutical composition according to claim 27, wherein the amount of said phenytoin species is about 5% to about 90% by weight of the pharmaceutical composition.

32. The pharmaceutical composition according to claim 27, wherein the amount of said phenytoin species is about 30 mg to about 100 mg.

33. The pharmaceutical composition of claim 27, wherein said composition is in the form of pellets, slugs, granules, spheroids, beads, or combinations thereof.

34. The pharmaceutical composition of claim 27, wherein said composition is in the form of tablets and capsules.

35. The pharmaceutical composition of claim 27, wherein said composition is a tablet in a capsule.

36. A pharmaceutical composition comprising a tablet in a capsule, wherein said tablet comprises a phenytoin species having the Raman shift as is set out in FIG. 2 in an erodible matrix and wherein said composition has the following in-vitro dissolution profile initially and after storage for 12 months at 25 degrees centigrade/60% relative humidity when measured in-vitro by dissolution testing:
  (a.) not more than 45 percent released in 30 minutes,
  (b.) between 40 and 80 percent released in 60 minutes,
  (c.) not less than 70 percent released in 120 minutes.

37. The pharmaceutical composition according to claim 36, wherein the amount of said phenytoin species is about 5% to about 90% by weight of the tablet.

38. The pharmaceutical composition according to claim 36, wherein the amount of said phenytoin species is about 15% to about 75% by weight per tablet.

39. The pharmaceutical composition according to claim 36, wherein the matrix is comprised of about 1% to about 35% by weight binder(s), of about 65% to about 99% by weight diluent(s), and of about 0% to about 10% by weight alkaline pH modifier(s).

40. The pharmaceutical composition according to claim 36, wherein said binder is a combination of about 5% to about 13% by weight povidone and about 1% to about 12% by weight hydroxyethyl cellulose; said diluent is about 65% to about 86% by weight microcrystalline cellulose; and said alkaline pH modifier is about 1% to about 10% by weight magnesium oxide.

41. A method for the treatment of epilepsy comprising administering the pharmaceutical composition according to claims 1, 20, 26, 27, or 36 to a human suffering from epilepsy.

42. A process for the preparation of the pharmaceutical composition of claims 11, 25, 26, or 40 comprising:
  (a.) preparing a binder solution by dissolving the povidone in an appropriate amount of solvent,
  (b.) blending the phenytoin sodium, the hydroxyethyl cellulose, the microcrystalline cellulose, and the magnesium oxide into a mixture,
  (c.) granulating said mixture with said binder solution to get a granulation,
  (d.) drying the granulation,
  (e.) add other pharmaceutical excipients to the granulation, then blend,
  (f.) tableting said granulation, and
  (g.) encapsulating said tablet.

43. A phenytoin species having the Raman Shift as set out in FIG. 2.

44. A method of preparing the species of claim 43 comprising:
  (a.) preparing an aqueous solution of a binder in about 31 mg to about 61 mg of water per 100 mg phenytoin species to be made,
  (b.) blending phenytoin sodium, binder, and/or diluent to form a mixture,
  (c.) granulating said mixture with said aqueous solution to get a granulation,
  (d.) drying the granulation, and
  (e.) milling and blending the granulation.

* * * * *